United States Patent
Takayama et al.

(10) Patent No.: US 7,740,626 B2
(45) Date of Patent: Jun. 22, 2010

(54) LASER INDUCED LIQUID JET GENERATING APPARATUS

(75) Inventors: Kazuyoshi Takayama, Sendai (JP); Takayuki Hirano, Sendai (JP); Atsuhiro Nakagawa, Sendai (JP); Hideshi Obitsu, Fuji (JP); Shigeru Omori, Hadano (JP); Takeshi Kanamaru, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1617 days.

(21) Appl. No.: 10/989,406

(22) Filed: Nov. 17, 2004

(65) Prior Publication Data

US 2005/0124985 A1  Jun. 9, 2005

(30) Foreign Application Priority Data

Nov. 21, 2003  (JP) ............................. 2003-392130
Nov. 21, 2003  (JP) ............................. 2003-392133

(51) Int. Cl.
*A61B 18/20* (2006.01)

(52) U.S. Cl. ................................. 606/15; 606/7; 606/23

(58) Field of Classification Search ............... 606/7, 606/13–16, 20–23; 607/88, 89, 92, 104
See application file for complete search history.

(56) References Cited

U.S. PATENT DOCUMENTS

| 4,597,380 | A | * | 7/1986 | Raif et al. ................. 600/108 |
| 4,690,672 | A |   | 9/1987 | Veltrup |
| 5,203,781 | A | * | 4/1993 | Bonati et al. ................ 606/15 |
| 5,562,692 | A |   | 10/1996 | Bair |
| 6,022,309 | A |   | 2/2000 | Celliers et al. |
| 6,117,128 | A | * | 9/2000 | Gregory ..................... 606/7 |
| 6,406,486 | B1 |  | 6/2002 | De La Torre et al. |
| 6,440,124 | B1 | * | 8/2002 | Esch et al. .................. 606/7 |
| 6,547,779 | B2 | * | 4/2003 | Levine et al. ................ 606/7 |
| 6,913,605 | B2 |  | 7/2005 | Fletcher et al. |
| 7,344,528 | B1 | * | 3/2008 | Tu et al. ..................... 606/7 |

FOREIGN PATENT DOCUMENTS

| JP | H5-285150 A | 11/1993 |
| JP | H7-313520 A | 12/1995 |
| JP | 2000-508938 T | 7/2000 |
| JP | 2003-500098 T | 1/2003 |
| JP | 2003-111766 | 4/2003 |
| WO | 00/04838 | 2/2000 |

OTHER PUBLICATIONS

T. Hirano et al., "Fibrinolysis with Ho:YAG laser-induced liquid jet"; Journal of Japan Society for Laser Surgery and Medicine, vol. 22, No. 3, 2001, with English translation.
European Search Report dated Feb. 11, 2005.
Official Action (Notice of Reason for Refusal) issued on Aug. 12, 2008 in corresponding Japanese Application No. 2003-392133, and English-language translation of Official Action.

* cited by examiner

*Primary Examiner*—Ahmed M Farah
(74) *Attorney, Agent, or Firm*—Buchanan Ingersoll & Rooney PC

(57) ABSTRACT

The laser induced liquid jet generating apparatus irradiates a laser beam on a liquid in a main body, guides the generated liquid jet into a catheter via a nozzle, and generates a flow in the direction opposite the liquid jet. Even by the use of a catheter having a small outside diameter, therefore, the apparatus is enabled to effect powerful laser irradiation without being thermally affected by the laser beam and consequently shatter thrombus, for example, and recover by aspiration the shattered thrombus through the distal end of the catheter.

16 Claims, 9 Drawing Sheets

LASER INDUCED LIQUID JET GENERATING APPARATUS

CROSS-REFERENCE TO RELATED APPLICATIONS

This application is based upon Japanese Patent Applications No. 2003-392130 and No. 2003-392133 filed Nov. 21, 2003 the contents of which are hereby incorporated by reference.

BACKGROUND OF THE INVENTION

1. Field of the Invention

This invention relates to a laser induced liquid jet generating apparatus which serves the purpose of irradiating a laser beam against a liquid thereby generating a liquid jet flow and utilizing the jet flow to shatter a target object such as thrombus, and recovering the shattered object.

2. Description of the Related Art

In recent years, as a means to cure the thrombosis which obstructs the human blood vessel, the method which consists in generating a liquid jet flow with a laser beam and physically breaking the clot with the jet flow is prevailing. This method has been awakening a great expectation for the therapy of the thrombosis because it promises early resumption of the blood flow without requiring administration of a large amount of a thrombus-dissolving agent which brings a serious secondary effect. Particularly, when the cerebral tissue remains in the state of ischemia for not less than six hours, it is held that the restoration from the neuropathic symptom is difficult to attain. When the blood flow recurs in a few hours after the crisis, the method brings a very high curative effect.

The official gazette of JP-A-2003-111766, WO00/04838 (the official gazette of International Unexamined Patent Publication No. 2002-521084), and THE JOURNAL OF JAPAN SOCIETY FOR LASER SURGERY AND MEDICINE, Vol. 22, No. 3 (2001) (refer to page 217) describe a technique which comprises guiding a laser in a pulsating form from a laser oscillator into an optical fiber inserted in a catheter, abruptly heating a physiological saline filling the catheter interior and inducing a liquid jet flow, and shattering and removing the thrombosis by dint of the liquid jet flow.

Since this method guides the catheter having the optical fiber inserted therein close to the thrombosis, for example, and generates the liquid jet flow and, therefore, enables the power of the liquid jet flow to reach the thrombosis without any decline of the power, it is capable of acquiring a high therapeutic effect.

The catheter to be inserted into the blood vessel is very slender. Further, when it is used in the state of having an optical fiber inserted therein, it keeps the optical fiber itself from increasing its thickness, imposes a limit on the intensity of the laser beam, and renders irradiation of a powerful laser beam difficult. The method, therefore, is possibly incapable of generating a powerful liquid jet flow and effecting necessary shattering of the target object such as the thrombosis, for example, sufficiently.

The conventional catheter is a long slender tube formed of vinyl chloride or PCB (poly-chlorobiphenyl) or, as disclosed in WO00-04838 (the official gazette of International Unexamined Patent Publication No. 2002-521084), of such a material as polypropylene or polyimide. Since it is soft throughout the entire volume so as to be deformed along the meandering blood vessel, it tends to be thermally affected when it is exposed to a powerful laser beam.

Particularly, when the optical fiber having an outside diameter (core diameter) of about 0.4 mm is inserted into a catheter of a small diameter (generally about 0.9 mm), only an extremely small gap is allowed to exist between the inner surface of the catheter and the outer surface of the optical fiber. When they are exposed to a powerful laser beam, the heat of the laser beam is conducted to the catheter and the catheter is consequently fused and deformed and made to obstruct smooth discharge of a liquid jet flow and curtail its own service life.

Further, since the catheter of this nature is only capable of shattering the target object such as the thrombus but is devoid of a means to recover the shattered target object, the thrombus which has been shattered is suffered to float in the blood vessel. When the floating fragments of the thrombus happen to get caught in the blood vessel, they will possible form a main cause for the generation of a new thrombus. It is conceivable to provide the catheter used exclusively for shattering the thrombus with a separate tube used exclusively for absorbing the thrombus. When these catheter and tube are inserted into the blood vessel, they bring the disadvantage of aggravating the burden imposed on the human body.

SUMMARY OF THE INVENTION

This invention provides a laser induced liquid jet generating apparatus which is capable of inducing irradiation with as powerful laser beam as possible even in a slender catheter without being thermally affected by the laser beam, permitting protracted use as well, and enjoying a smooth operation.

This invention also provides a laser induced liquid jet generating apparatus which is capable of recovering the target object such as the thrombus which has been shattered by the liquid jet without adding to the burden imposed on the human body.

The laser induced liquid jet generating apparatus of this invention is characterized by being provided with a main body possessing a spatial part in the interior thereof, an optical fiber fitting part so disposed as to communicate with the spatial part of the main body and adapted to fit an optical fiber furnished in the leading terminal thereof with a laser irradiating part for guiding the laser beam from a laser oscillator, a liquid injecting part for injecting a prescribed liquid for absorbing the laser beam into the spatial part of the main body, and an injection nozzle for spouting to the exterior of the main body a liquid jet flow generated by irradiating the laser beam toward the liquid and by being adapted to guide the jet spouted through the nozzle toward a catheter.

The apparatus contemplated by this invention shuns irradiation of a laser beam in a slender and narrow catheter, irradiates the laser beam in a large spatial part forming the interior of a main body, and introduces the generated liquid jet flow through a nozzle into a catheter. Consequently, it allows use of a slender catheter, avoids being thermally affected by the laser beam, attains irradiation of as powerful laser beam as possible, permits a protracted use, and realizes a smooth operation. As a result, it is capable of infallibly shattering the target object such as the thrombus very powerfully.

By injecting the liquid via the liquid injecting part toward the laser irradiating part of the optical fiber, it is made possible to exalt the effect of cooling the laser irradiating part of the optical fiber and add to the powerfulness with which the laser beam is irradiated.

The laser induced liquid jet generating apparatus contemplated by this invention is also characterized by generating a flow opposite the liquid jet flow in the catheter, aspirating the shattered target object from the distal end portion of the catheter, and removing it from the interior of the blood vessel.

According to the apparatus of this invention, since it generates the flow opposite the liquid jet flow, the target object can be recovered as carried on the flow through the catheter and the generation of a new thrombus with the shattered thrombus is precluded.

Further, the apparatus allows one catheter to fulfill the function of shattering the target object and the function of recovering the shattered target object, attains the exaltation of the operating property, and brings the advantage of lessening the burden imposed on the human body as compared with the apparatus requiring provision of a separate tube.

DETAILED DESCRIPTION OF THE INVENTION

Now, the embodiments of this invention will be described in detail below with reference to the drawings.

First Embodiment

Figure 1:
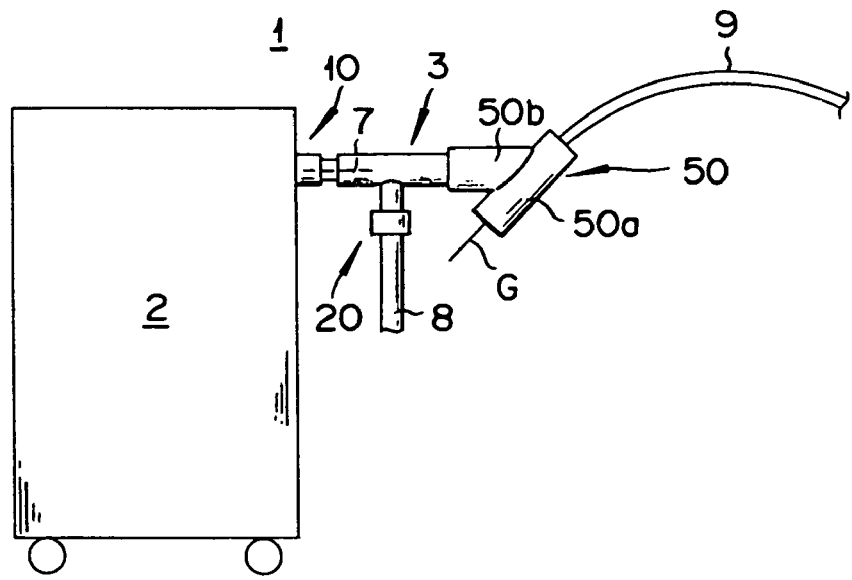
FIG. 1 is a schematic front view illustrating the whole of the first embodiment of this invention.
Figure 2:
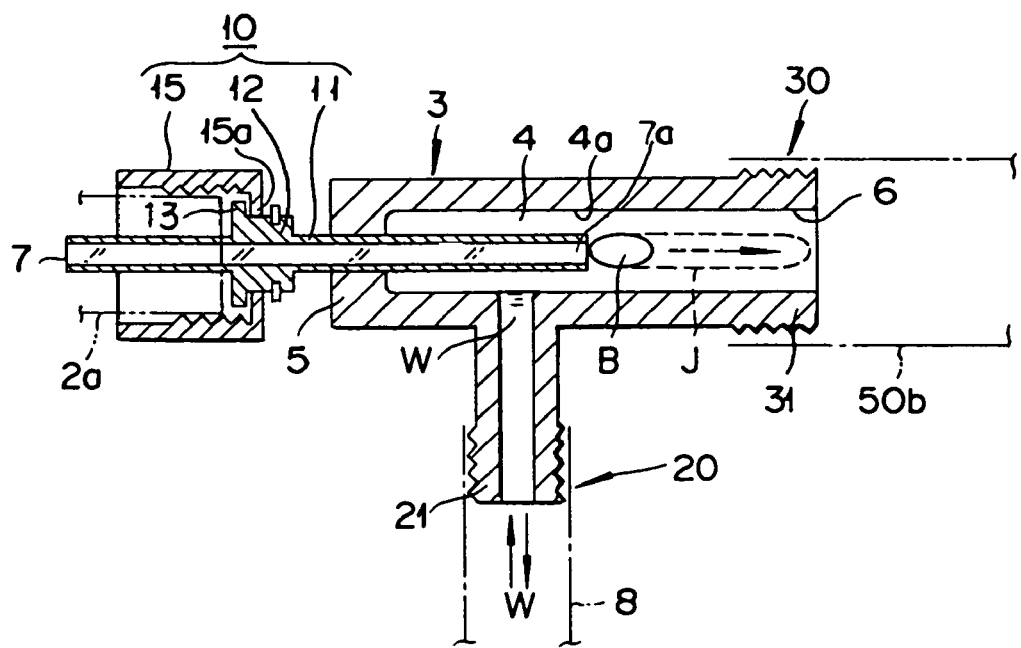
FIG. 2 is a magnified cross section of the essential part of FIG. 1.
Figure 3:
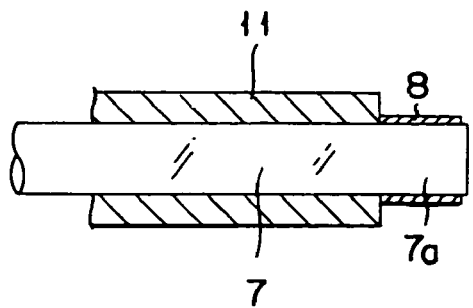
FIG. 3 is a cross section illustrating the leading terminal part of an optical fiber.

The first embodiment illustrated in FIG. 1 and FIG. 2 is a laser induced liquid jet generating apparatus 1 for curing the thrombosis which is a disease of forming a blood clot within a man's blood vessel. This apparatus 1 generally comprises a main body 3 connected to a laser oscillator 2, an optical fiber fitting part 10 made to communicate with the main body 3, a liquid injecting part 20 for injecting a prescribed liquid W into a spatial part 4 (refer to FIG. 2) of the main body 3, and a Y-shaped Y connector part 50 disposed at the leading terminal part (the leading terminal side of a ferrule 11) of the optical fiber fitting part 10.

Since the laser oscillator 2 is a thing well known already, the explanation thereof will be omitted. The main body 3 is a kind of coupler furnished with various members as shown in FIG. 2. The main body 3 is formed of a material possessing a high melting point enough to withstand the heat emitted by an optical fiber 7 together with stiffness such as, for example, a metal like stainless steel or aluminum alloy and provided in the interior thereof with the slender spatial part 4 describing a circular cross section and extending straightly. The spatial part 4 has one end thereof closed with a terminal wall 5 and the other end thereof opened to form a spouting nozzle 6.

To the terminal wall 5 of the spatial part 4, the optical fiber fitting part 10 is connected. The optical fiber fitting part 10 comprises the tubular ferrule 11 provided in the interior thereof with a slender passage for allowing insertion of the optical fiber 7 therethrough, an engaging member 12 disposed integrally at the intermediate position of the ferrule 11, and a female screw cap 15 for engaging a flange 13 of the engaging member 12 and an engaging piece 15a. The female screw cap 15 is helically joined with a male screw projecting part 2a on the laser oscillator 2 side. By this helical union, the optical fiber fitting part 10 is fixed to the laser oscillator 2. Incidentally, the optical fiber 7 (indicated by a broken line in FIG. 1) is also retained as fixed in position by the helical union between the female screw cap 15 and the screw projecting part 2a. Optionally, it may be provided with a separate optical fiber fixing part.

The leading terminal side of the ferrule 11 is inserted through the terminal wall 5 and projected into the spatial part 4. The optical fiber 7 is inserted into and fixed in the ferrule 11. The leading terminal of the optical fiber 7, namely a laser irradiating part 7a, is projected out of the ferrule 11 and adapted to irradiate therefrom in a pulsated form a laser of a wavelength easy to be absorbed by a liquid W. The outer periphery of the laser irradiating part 7a is preferred to be coated with a thin metallic film 8 as by plating means with a view to enhancing the mechanical strength of a laser irradiating part 7a itself and exalting the durability thereof.

Though the laser irradiated from the laser irradiating part 7a possesses the property of producing rectilinear propagation, it is permissible to form a light reflecting layer (not shown) which is capable of reflecting a laser beam. By forming the light reflecting layer of this nature, it is made possible to prevent the irradiated laser beam from being absorbed by the main body, exalt the efficiency of utilization of the laser beam, and consequently heighten the powerfulness of the liquid jet flow. This light reflecting layer is formed by treating the inner surface of the main body 3. As preferred examples of the method for the treatment of the inner surface, the coating by the DLC (diamond like carbon), the ceramic coating, and the coating with gold or silver may be cited.

The liquid injecting part 20 contemplated by the present embodiment is a tubular member provided in the interior thereof with a passage for allowing flow of the liquid W therethrough and having a terminal part thereof transformed by the formation of a screw thread into a connecting part 21. A tube 8 is connected to the connecting part 21 and adapted to have the prescribed liquid W injected therein by means of a syringe pump (not shown). The position of the liquid injecting part 20 is preferred to be such that the liquid W may be directed toward the laser irradiating part 7a of the optical fiber 7 and the laser irradiating part 7a consequently may be infallibly cooled. It is further preferred to be more directed toward the rear terminal side than the laser irradiating part 7a at the leading terminal of the ferrule 11, namely toward the terminal wall 5 side, as shown in FIG. 2. So long as the position is such as this, the laser irradiating part 7a is infallibly cooled because the liquid W flows out while it keeps contact with the laser irradiating part 7a.

The liquid W is what results from adding a small amount of a thrombus dissolving agent to the physiological saline, for example, which is capable of being gasified by absorbing the energy of the laser beam. The liquid is partly gasified by absorbing the energy of the laser beam, this gasification gives rise to an air bubble (bubble B) shown in FIG. 2, and the sudden inflation of the bubble B causes the liquid W to be spouted in the form of the so-called liquid jet flow J through the nozzle 6 formed in a terminal part 30 of the main body 3.

The jet spouted through the nozzle 6 is guided to the catheter 9. In this embodiment, it is guided through the medium of the Y connector part 50 disposed as connected to the nozzle 6.

Since the Y connector part 50 is a device already well known, a detailed description thereof will be omitted. It is furnished in the interior thereof with a tubular elastic body and is provided with a compressing member for deforming the elastic body by compression and provided further with a first port 50a and a second port 50b which respectively communicate with the ambience. A guide wire G is inserted into the first port 50a. The guide wire G is watertightly fixed by deforming the elastic body in the first port 50a by compression. The catheter 9 is watertightly connected to the other terminal part of the first port 50a. The second port 50b is watertightly connected to a connecting part 31 produced by forming a screw thread in the terminal part 30 of the main body 3.

The nozzle 6 is positioned opposite the optical fiber fitting part 10 which is provided for the main body 3. This is because the power of the liquid jet flow J generated in the laser irradiating part 7a is required to be guided easily into the catheter 9 through the medium of the Y connector part 50.

The catheter 9 is a tube which is wholly slender and flexible and possesses strength in order that it may be easily inserted even into a slender meandering blood vessel.

The material possessing flexibility and strength, for example, is a HDPE (high density polyethylene) monolayer or a LLDPE (linear low density polyethylene) bilayer. Not only these but also polyolefins such as polyvinyl chloride, polyethylene, polypropylene, ethylene-propylene copolymer, and ethylene-vinyl acetate copolymer, polyesters such as polyethylene terephthalate and polybutylene terephthalate, various thermoplastic resins and thermosetting resins such as polystyrene, polyurethane, polyamide, polyimide, polyoxymethylene, polyvinyl alcohol, polytetrafluoroethylene, polyvinylidene fluoride, and other fluorine type resins, thermoplastic elastomers such as polyamide elastomer and polyester elastomers, and various rubbers such as silicone rubber and latex rubber are available.

The catheter 9 contemplated by this embodiment is extremely advantageous from the viewpoint of the insertion thereof into the blood vessel because it is not furnished in the interior thereof with an optical fiber 7 and, therefore, can be formed in the smallest possible thickness.

Now, the operation of this embodiment will be described below.

First, the artisan fixes the main body 3 by helically joining the female screw cap 15 of the optical fiber fitting part 10 having the optical fiber 7 inserted in advance in the ferrule 11 thereof and the screw projecting part 2a thereby fixing the optical fiber fitting part 10 to the laser oscillator 2.

Then, he connects the tube 8 for supplying the liquid W to the connecting part 21 of the liquid injecting part 20 and connects the catheter 9 to the connecting part 31 of the main body terminal part 30 through the medium of the Y connector part 50. Thereafter, he feeds the liquid W as with a syringe pump, for example, to the spatial part 4 of the main body 3 and fills it. He finds whether or not the liquid W has filled the spatial part 4 to capacity by visually confirming the discharge of the liquid through the distal end of the catheter 9.

In the state, the artisan inserts the guide wire G through the first port 50a of the Y connector part 50 and, when the distal end thereof reaches the site of a thrombus, keeps the guide wire G at that position. Then, he inserts the catheter 9 into the blood vessel with the guide wire G as the guide. In this case, when he has the catheter 9 in advance provided at the distal end portion thereof with a radiopaque material (such as, for example, gold, silver, platinum, tungsten, palladium, or alloys thereof) as a so-called marker, he is enabled to insert the catheter 9 while he keeps the position of the marker confirmed as by radiation of X rays. Thus, he is allowed to comprehend the position of the catheter 9 exactly in the live human body.

When the distal end of the catheter 9 reaches the prescribed side in the blood vessel, he extracts the guide wire G from the catheter 9. When he then sets the laser oscillator 2 operating, the pulsated laser beam is irradiated from the laser irradiating part 7a at the leading terminal of the optical fiber toward the liquid W.

This irradiation is carried out in the main body 3 and not in the catheter as in the conventional apparatus. The irradiation is destined to exert a high temperature and the pressing power due to the sudden generation of bubble B to bear on the main body 3. In this embodiment, since the main body 3 is formed of a metal, it is capable of resisting even quite a powerful pulsating laser beam. Thus, the powerful pulse laser beam can be irradiated without either entailing the problem of suffering the high temperature to deform the catheter 9 or exposing the catheter 9 to direct heating.

In consequence of the irradiation of the pulsated laser beam, the liquid W is suddenly heated and the bubble B is intermittently generated. By the bubble B, the liquid W in the chamber 13 is suddenly pressed and expelled, with the result that the liquid jet flow J will be provided.

In this embodiment, since the laser irradiating part 7a at the leading terminal of the ferrule 11 is positioned opposite the nozzle 6, the produced liquid jet flow J is promptly spouted through the nozzle 6 of the main body 3 and directed toward the catheter 9 through the first port 50a of the Y connector part 50.

At this stage, since the main body 3 and the catheter 9 are filled with the liquid W, the power of the liquid jet flow J is transmitted through the medium of the liquid W in the main body 3 and the liquid W in the catheter 9 and directed toward the distal end portion of the catheter 9.

As a result, the liquid W in the catheter 9 is spouted through the distal end thereof toward the thrombus lying ahead and the thrombus in the blood vessel is shattered by collision with the powerful liquid jet flow and by assistance of a thrombus dissolving agent. Then, in the blood vessel, the reflux of the blood is eventually started again.

The thrombus shattered as described above can be extracted out of the blood vessel together with the liquid by means of a sucking tube connected to the liquid injection part 20.

Second Embodiment

Figure 4:
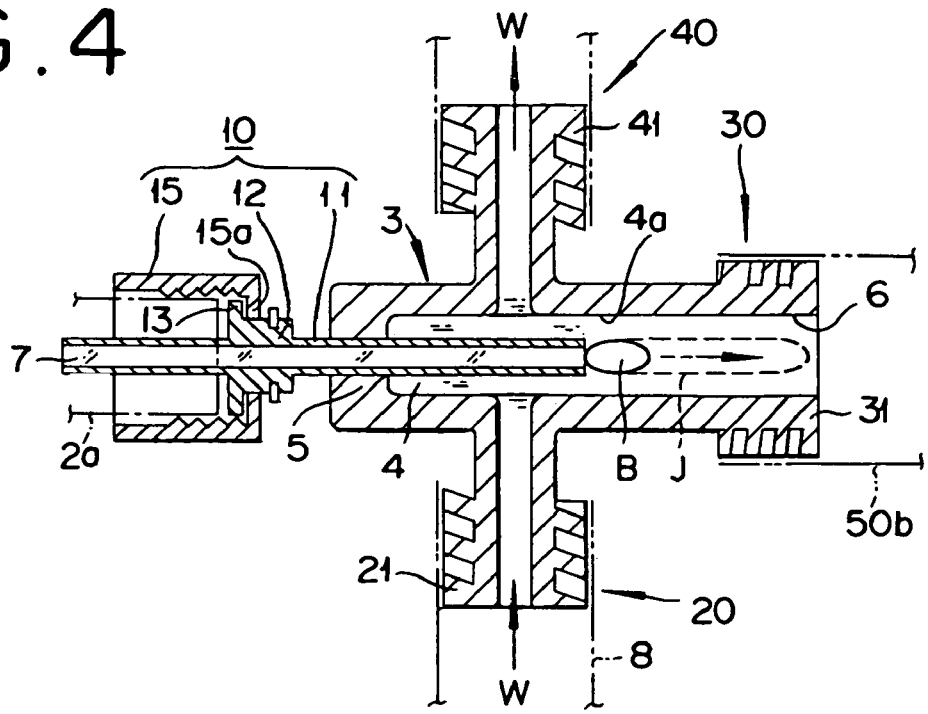
FIG. 4 is a cross section of a main body illustrating a second embodiment of this invention.

While the first embodiment utilizes the liquid injecting part 20 for extracting the shattered thrombus, the second embodiment illustrated in FIG. 4 contemplates generating a flow opposite the liquid jet flow, aspirating the shattered target substance from the distal end of the catheter 9, and removing it from within the blood vessel. Specifically, a liquid discharging part 40 is disposed opposite the liquid injecting part 20 of the main body 3 and it is utilized for generating the flow opposite the liquid jet flow. The same members as shown in FIG. 1 and FIG. 2 will be denoted here by the same reference numerals and their explanation will be omitted.

The liquid discharging part 40 is provided with a connecting part 41 having a screw tread formed in the terminal part thereof and is possessed of a passage in the interior thereof. It is connected to a suction pump, for example, through the medium of a hose. By the operation of this suction pump, it is enabled to discharge the liquid W which contains the shattered thrombus.

The second embodiment, because of the ability to carry out the injection and the discharge of the liquid W independently without requiring replacement of the pump or the liquid injecting tube 8, is enabled to enhance the efficiency of operation, smoothen the flow of the liquid W in the main body 3, increase the flow volume of the liquid W as well, and consequently exalt the effect of cooling the laser irradiating part 7a.

Third Embodiment

Figure 5:
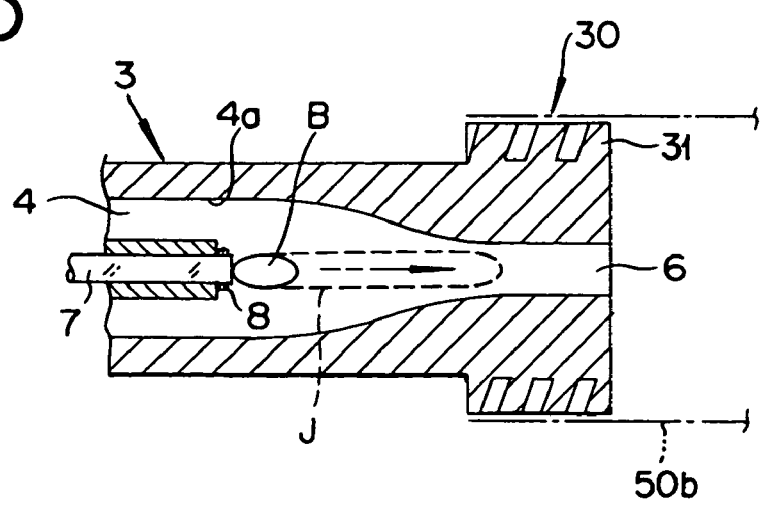
FIG. 5 is a cross section of the essential part of the main body illustrating a third embodiment of this invention.

In the first and second embodiments, the spatial part 4 of the main body 3 has an inner wall surface 4a thereof formed nearly straight from the optical fiber fitting part 10 toward the nozzle 6. The inner wall surface 4a may be alternatively formed as tapered so that the inner diameter of the spatial part 4 decreases toward the leading terminal as shown in FIG. 5.

By thus tapering the inner wall surface 4a, the speed of flow of the liquid jet J induced by the laser irradiating part 7a is further heightened by the tapered spatial part 4 and the shattering is attained more powerfully. Moreover, when the spatial part 4 is in the tapered shape, it constitutes a guide and enables the power of the liquid jet flow to be smoothly introduced into the catheter 9.

Fourth Embodiment

Figure 6:
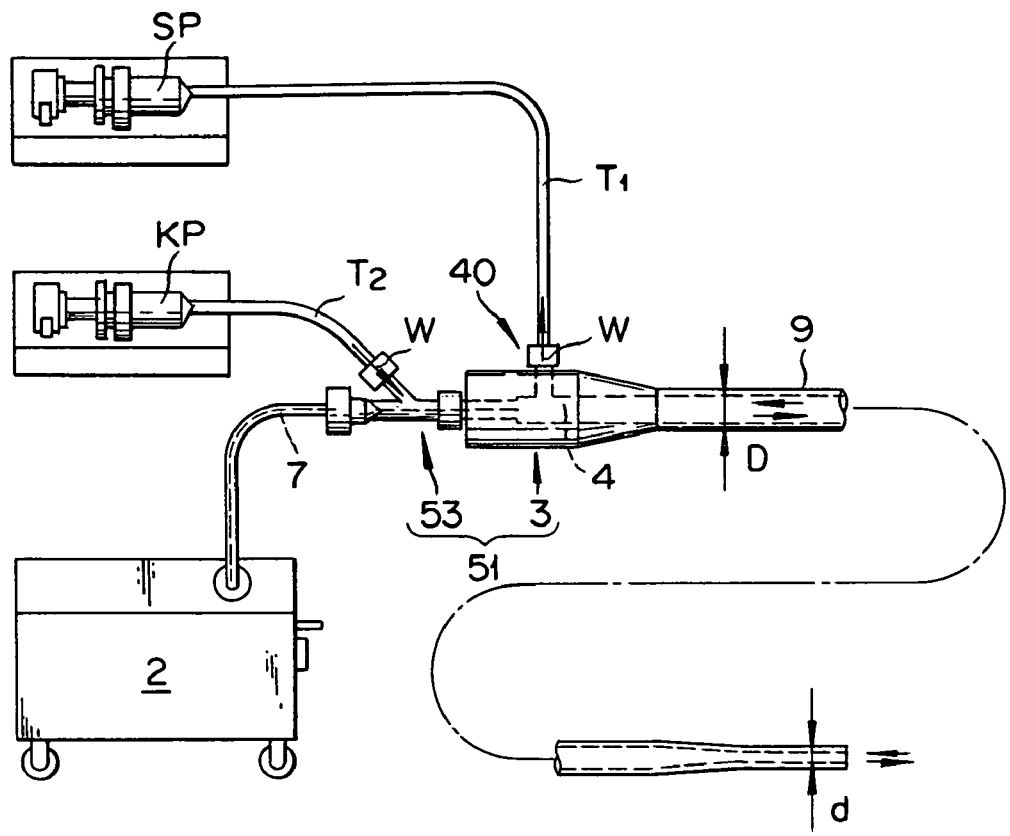
FIG. 6 is a schematic front view illustrating the whole of the fourth embodiment of this invention.

The fourth embodiment illustrated in FIG. 6, instead of carrying out the injection and the discharge of the liquid W in the main body 3, contemplates carrying out the operations of injection and discharge at separate positions with a view to facilitating the artisan's nearby operation. To be specific, the apparatus of this embodiment is provided with a nearby operating part 51 which has detachably concatenated serially a main body 3 and a Y connector 53. The main body is possessed of a liquid discharging part 40 and the Y connector 53 is possessed of an optical fiber fitting part 10 connected to the rear terminal of the main body 3 and a liquid injecting part 20.

In other words, the present apparatus comprises a first main body (main body 3) and a second main body (Y connector 53) capable of being connected to the rear terminal part of the first main body. The first main body (main body 3) is possessed of a first spatial part 4 formed in the interior thereof, a liquid discharging part 40 communicating with the spatial part 4 and used for discharging the liquid in the spatial part 4, a nozzle 6 disposed in the leading terminal part of the first main body (main body 3) and spouting the liquid in the spatial part 4 to the exterior of the first main body (main body 3), and a first connecting part 35 disposed in the rear terminal part of the first main body (main body 3) and furnished with a first opening part 35a communicating with the first spatial part 4.

The second main body (Y connector 53) is furnished with a second spatial part 53a formed therein and a second opening part 58a disposed at the leading terminal part of the second main body (Y connector 53) and communicating with the spatial part 53a and is possessed of a second connecting part 58 (coupler) capable of being connected to the first connecting part 35 in a state allowing communication between the first spatial part 4 and the second spatial part 53, an optical fiber fitting part 10 disposed in a state capable of communicating with the spatial part 53a, and a liquid injecting part 20 for injection the liquid W into the spatial part 53a.

The apparatus will be described in further detail below. The members fulfilling the same functions as shown in FIGS. 1-4 will be denoted by the same referential numerals and the explanation thereof will be omitted.

Figure 7:
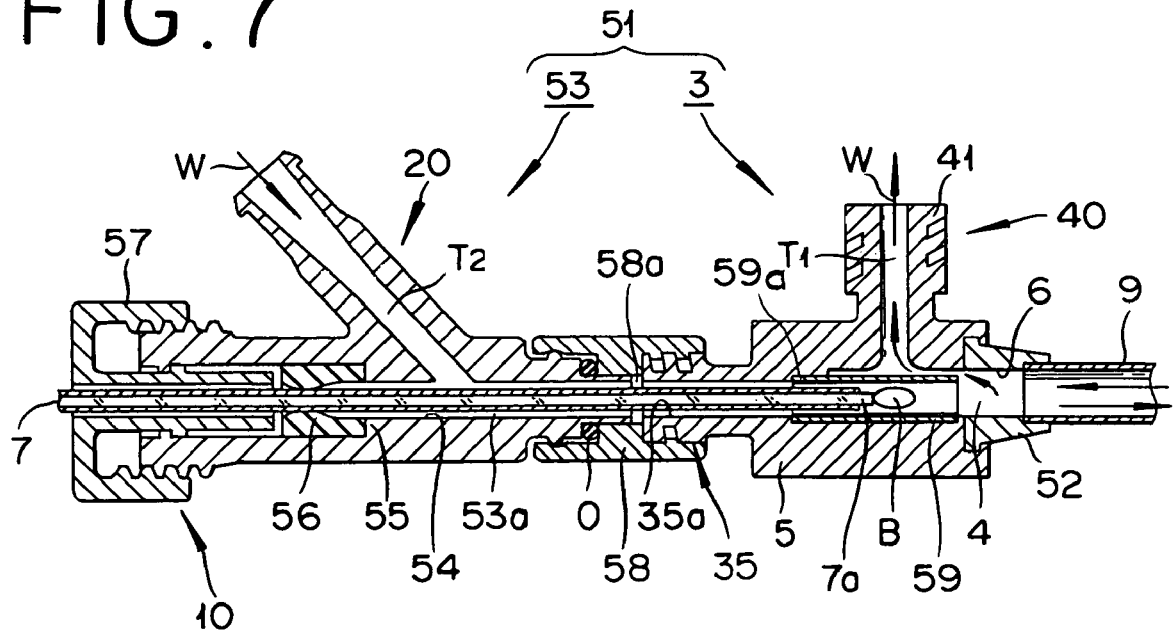
FIG. 7 is a magnified cross section of the essential part of FIG. 6.

The first main body (main body 3) forms the first spatial part 4 which has the leading terminal part of the optical fiber 7 disposed in the interior thereof in the same manner as the preceding embodiment as illustrated in FIG. 7. The catheter 9 is connected to the leading terminal of the first spatial part 4 through the medium of a connector 52. A discharge passage T1 directed upwardly also communicates with the intermediate part of the first spatial part 4. The discharge passage T1 is intended to discharge the liquid W containing the shattered thrombus, for example and is enabled to discharge the liquid W by dint of a suction pump SP such as, for example, a syringe pump (refer to FIG. 6), which is connected to the liquid discharging part 40.

The laser irradiating part 7a in the leading terminal part of the optical fiber 7 is disposed in the neighborhood of the discharge passage T1. This neighborhood is provided with a reinforcing member, specifically a metallic partitioning tube 59, which is formed of a material having a high melting point enough to with stand the heat emitted by the optical fiber 7 and possessing as well prescribed stiffness. The partitioning tube 59 is possessed of the function of efficiently spouting the liquid jet flow J of bubble B generated by the laser irradiating part 7a through the nozzle 6 of the first main body (main body 3), the function of dividing the flow path of the liquid jet flow J and the flow path for allowing flow of the liquid W aspirated by the discharge passage T1, and the function of protecting and reinforcing the inner wall surface of the first spatial part 4. The partitioning tube 59, therefore, is preferred to be elongated more toward the nozzle 6 side than the basal part of the discharge passage T1.

The partitioning tube 59, however, is preferred to be so constructed that a proper gap may occur between the outer surface of the partitioning tube 59 and the basal part of the discharge passage T1 lest the elongation of the partitioning tube 59 should interfere with the flow of the liquid W into the discharge passage T1. The partitioning tube 59 is further preferred to be provided on the inner surface thereof with a reflecting layer 59a capable of reflecting the laser beam issued from the optical fiber 7.

Meanwhile, the second main body (Y connector 53) integrally communicates with the second spatial part 53a mentioned above and has formed therein a fiber passage 54 for selectively allowing the optical fiber 7 and the guide wire G to be inserted therethrough and a liquid injection passage T2 for supplying the liquid W. These two passages 54 and T2 intersect each other at a prescribed angle and form a confluence in the second spatial part 53a and communicate with the first spatial part 4 of the first main body (main body 3) through the medium of the opening part 35a.

The fiber passage 54 is provided in the neighborhood of the center thereof with a stepped part 55. One end of an elastic body 56 collides against this stepped part 55. The second main body (Y connector 53) is provided in the terminal part thereof with a screw cap 57. The screw cap 57, when moved in the axial direction, cooperates with the stepped part 55 to deform the elastic body 56 by compression and fix and retain watertightly the optical fiber 7 and the guide wire G.

A liquid feeding pump KP, specifically a syringe pump (refer to FIG. 6), is connected to the liquid injection passage T2. Then, the first main body (main body 3) and the second main body (Y connector 53) are connected to each other by means of a screw type second connecting part 58 (coupler) through the medium of an O-ring O.

Since the discharge passage T1 for discharging the liquid W and the liquid injection passage T2 for supplying the liquid W are independently disposed at separated positions as described above, the apparatus permits easy operation and prevents erroneous operation.

Now, the operation of this embodiment will be described below.

First, the artisan connects the catheter 9 to the leading terminal of the first main body (main body 3) through the medium of a connector 52 and connects the second main body (Y connector 53) to the rear terminal of the first main body (main body 3) through the medium of a screw type second connecting part 58. He connects the connecting part 41 of the liquid discharging part 40 to the suction pump SP through the medium of a tube and connects the liquid injection passage T2 of the second main body (Y connector 53) to the liquid supplying pump KP through the medium of a tube.

He then sets the liquid supplying pump KP operating to supply the liquid W to the catheter 9, namely to perform the so-called priming.

He inserts the guide wire G into the fiber passage 54. He inserts the guide wire G inside the catheter 9 via the second spatial part 53a, the opening part 58a of the first connecting part 35, the first spatial part 4, and the nozzle 6 till it protrudes from the distal end of the catheter 9.

He then inserts only the guide wire G preliminarily into the blood vessel. When the leading terminal thereof arrives at a position approximating closely to the target lesion such as, for example, the thrombus, he discontinues the insertion and retains the guide wire G at that position. During this insertion, he continues to confirm the position of the guide wire G in the living body by means of X ray radiation by keeping an eye on the radiopaque marker. He advances the catheter 9 along the guide wire G which has attained access in advance to the target lesion. Though the catheter 9 is wholly slender and flexible, it can be easily inserted by using the rigid guide wire G as a guide.

When the leading terminal of the catheter 9 arrives at the lesion, he extracts the guide wire G from the fiber passage 54. Subsequently, he inserts the optical fiber 7 into the fiber passage 54 and moves the screw cap 57 in the axial direction while the leading terminal part of the optical fiber 7 is set in the prescribed position inside the first spatial part 4 of the first main body (main body 3). Consequently, the elastic body 56 is deformed by compression and the optical fiber 7 is watertightly fixed and retained.

First, he sets the liquid supplying pump KP operating to supply the liquid W to the catheter 9. Subsequently, he aspirates the liquid W by means of the suction pump SP. During the course of the transfusion, he is required to pay due attention lest air bubble should occur in the catheter 9 or in the blood vessel.

While the supply and the suction of the liquid W by the operation of the two pumps are alternately performed, they are preferred to be performed intermittently. The amount of supply and the amount of suction of the liquid W are equal and fall in the range of 1.0 ml/min~15.0 ml/min, for example. In this embodiment, the two flows can be infallibly generated because the flow of the liquid jet J from the laser irradiating part 7a and the flow of the liquid W to be suctioned are divided by the partitioning tube 59.

The laser irradiation is initiated by connecting the optical fiber 7 to the laser oscillator 2 while the supply of the liquid W is continued as described above.

When the laser oscillator 2 is actuated, the pulsated laser beam is passed through the optical fiber 7 and irradiated on the liquid W. The irradiation is effected in the first main body (main body 3). When the liquid W is suddenly heated by the pulsated laser beam, the bubble B is intermittently generated, passed through the nozzle 6 of the first main body (main body 3), and spouted in the form of a violent liquid jet J.

Particularly in this embodiment, since the laser irradiation is effected in the partitioning tube 59, the liquid jet J do not decrease its power because it is restricted from being diffused outwardly and is efficiently spouted through the nozzle 6 of the first main body (main body 3). The inner surface of the partitioning tube 59 is fated to be exposed to the high heat and the pressing power due to the sudden generation of bubble B. In this embodiment, however, the prescribed performance can be retained for a long time because of the use of the partitioning tube 59 made of a metal or the like.

Incidentally, when the syringe pump which is a suction pump SP is filled to capacity with the liquid, the surgical operation in process is temporarily interrupted and the syringe pump is replaced with a new supply.

The liquid jet J is spouted through the nozzle 6 of the first main body (main body 3) and directed toward the catheter 9. Since the interior of the first main body (main body 3) and the interior of the catheter 9 are filled with the liquid W, the power of the liquid jet J is transmitted through the medium of the liquid W in the first main body (main body 3) and the liquid W in the catheter 9 and directed toward the distal end of the catheter 9.

The catheter 9, as illustrated in FIG. 6, is allowed to have a smaller inside diameter d in the distal end portion than the inside diameter D in the proximal part. This differentiation brings a favorable effect of heightening the speed of flow of the liquid jet J when this flow is spouted through the distal end portion of the catheter 9.

When the liquid jet J spouted intermittently collides against the thrombus lying ahead, the thrombus is shattered by the collision coupled with the action of the thrombus dissolving agent and the circulation of the blood in the blood vessel is started again.

Since the catheter 9 is carrying out the suction continuously, the shattered thrombus is taken into the catheter 9 from the blood vessel, returned to the first main body (main body 3), and taken out to the exterior from the liquid discharging part 40 together with the liquid W.

The blood aspirated during the suction of the liquid is diluted with the influent liquid W, passed through the gap between the partitioning tube 59 and the basal part of the discharge passage T1, and guided to the discharge passage T1. Thus, the apparatus retains the initial performance without exposing the blood of high concentration to the laser beam of the optical fiber 7, suffering the blood to adhere to the leading terminal of the optical fiber 7 and carbonize, and degrading the subsequent shattering function and aspirating function.

The laser irradiation is stopped when the resumption of the circulation of the blood is confirmed. For the purpose of ensuring the recovery of the shattered thrombus, however, it is favorable to continue the supply and the suction of the liquid for a prescribed length of time. Then, after the elapse of the prescribed length of time, the suction pump SP and the liquid supplying pump KP are stopped and the catheter 9 is extracted from the patient's body.

Fifth Embodiment

In the preceding embodiment, the insertion of a catheter resort solely to a guide wire as a guide. Optionally, the catheter may use a wire guide and a thick tube (hereinafter referred to collectively as "a guiding catheter").

When the catheter is to be inserted into the cerebral blood vessel, for example, the insertion is initiated in a large blood vessel like the femoral artery, advanced through the carotid artery, terminated in a fine cerebral blood vessel. By the mere use of a guide wire, the insertion of a fine catheter through such a route as this is difficult to accomplish.

When a fine blood vessel diverges from a thick blood vessel, therefore, the guiding catheter is inserted to the branch point and thereafter a fine catheter (which corresponds to the catheter 9 in the preceding embodiment and will be referred to hereinafter as "a micro-catheter") is inserted into the guiding catheter with the guide wire G as a guide. In the state, the micro-catheter is inserted into the fine blood vessel either as guided by the guide wire G or by itself. In this manner, the convenience obtained in inserting the micro-catheter to the fine cerebral blood vessel is exalted and the technique of the insertion is smoothed.

Incidentally, the relation between the guiding catheter and the micro-catheter in this embodiment corresponds to that between the guiding catheter Gc and the micro-catheter Mc illustrated in FIG. 8 which will be described specifically herein below. Thus, they will be omitted from the illustration here.

Sixth Embodiment

While the foregoing embodiment contemplate effecting the laser irradiation within the main body 3 thereby enabling the spouting power of the generated liquid et J to be transmitted through the medium of the liquid W and discharged through the distal end portion of the catheter 9, the liquid jet J may be optionally generated by guiding the optical fiber 7 to the neighborhood of the distal end portion of the catheter 9 and effecting the laser irradiation there.

Figure 8:
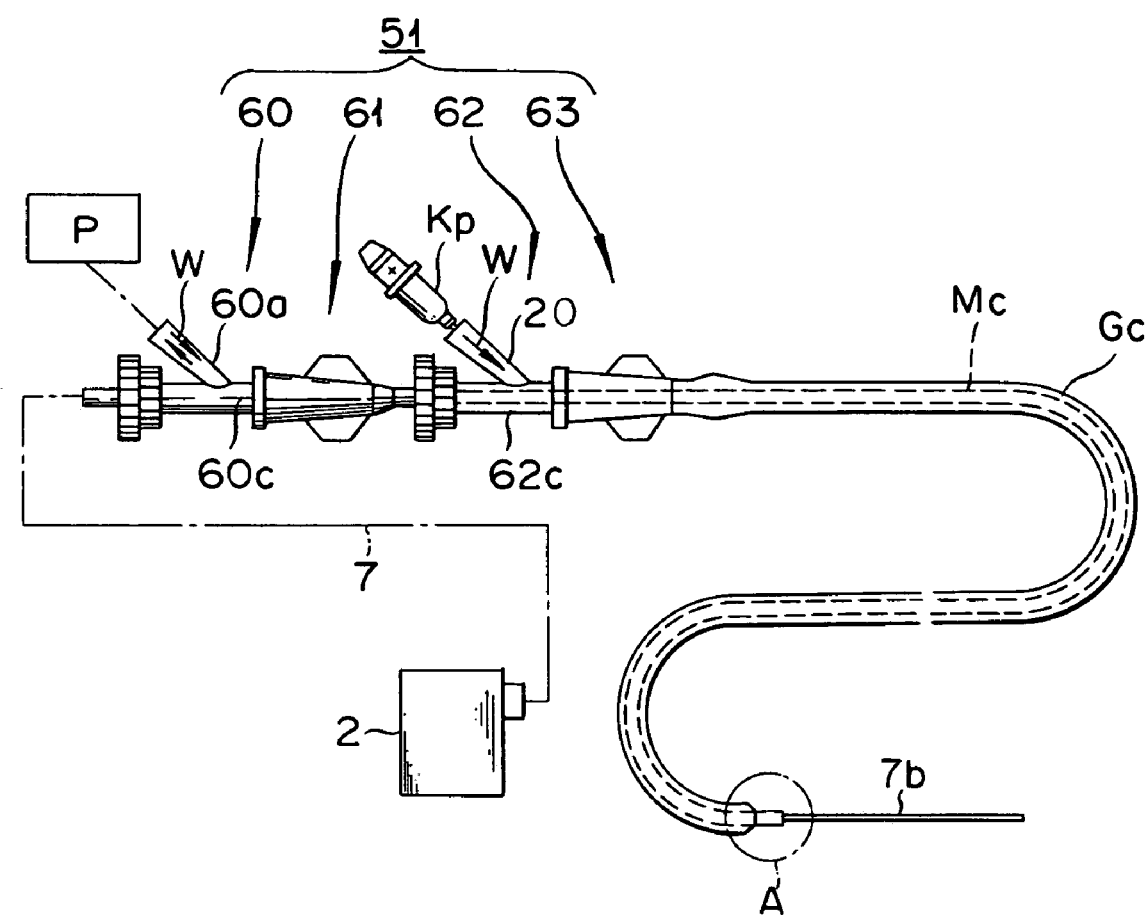
FIG. 8 is a schematic diagram illustrating the whole of the sixth embodiment of this invention.
Figure 9:
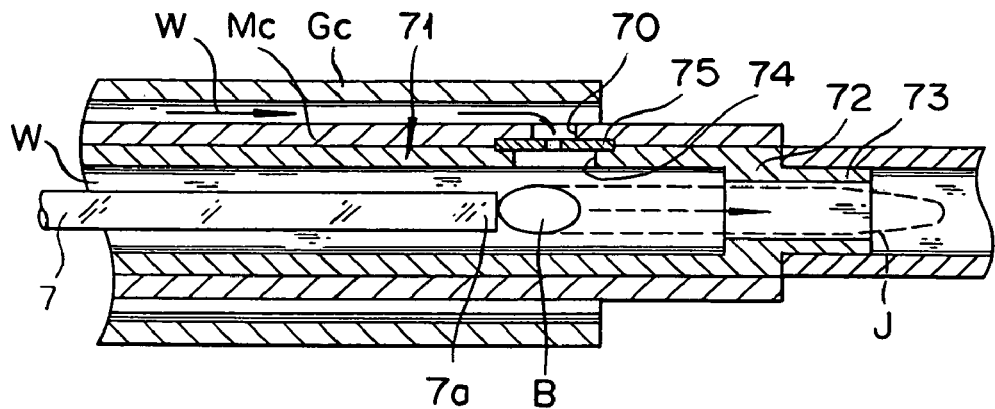
FIG. 9 is a magnified cross section of a part A of FIG. 8 during the generation of a liquid jet flow.
Figure 10:
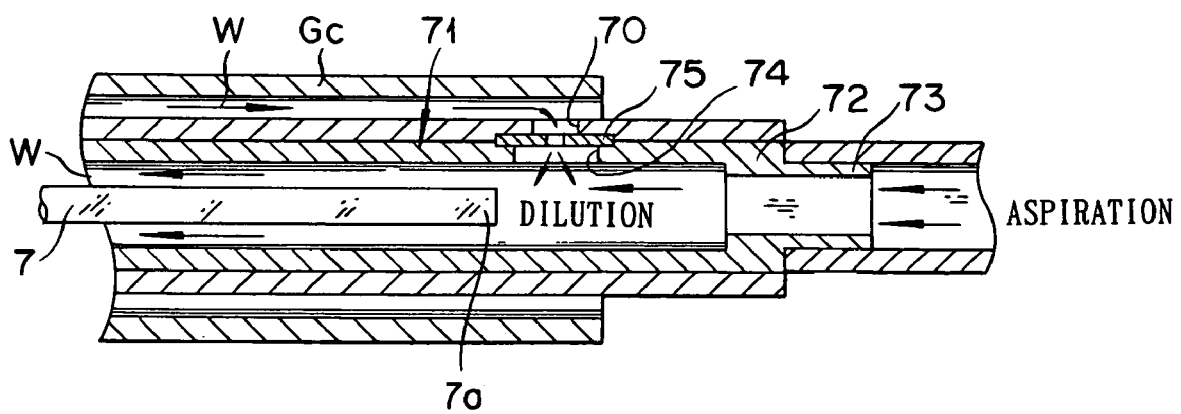
FIG. 10 is a magnified cross section of a part of FIG. 8 during the aspiration.

This embodiment is illustrated in FIG. 8 and FIG. 9. In these diagrams, the members fulfilling the same functions as shown in FIG. 1-FIG. 7 are denoted by the same reference numerals and their explanation will be omitted here.

In the apparatus illustrated in FIG. 8, a nearby operating part 51 which is operated by an artisan is composed of a Y connector 60, a hub 61, a Y connector 62, and a hub 63. These component parts are serially concatenated as mutually detachably.

The Y connector 60 is provided with a fiber passing part 60c allowing insertion therethrough of the optical fiber 7 guiding the laser beam from the laser oscillator 2 and retaining the optical fiber 7 at a fixed position and a passage 60a having connected thereto a pump P fulfilling the function of filling the micro-catheter Mc with the liquid W and the function of aspirating the liquid W which has contained the shattered thrombus.

The hub 61 communicates with the Y connector 60 and has the micro-catheter Mc fitted to the leading terminal thereof.

The Y connector 62 is provided with a catheter retaining part 62c possessed of an elastically compressive deformed body watertightly fixing the micro-catheter Mc inserted in the interior thereof and a liquid injecting part 20 for injecting the liquid W by the syringe pump Kp to the interior of the guiding catheter Gc, namely to the gap between the micro-catheter Mc and the guiding catheter Gc.

The hub 63 has the proximal end portion of the guiding catheter Gc attached thereto.

The micro-catheter Mc is opened a lumen therein and intended to fulfill the function of a supply passage for the liquid W and a passage for recovering the shattered thrombus, and the function of a passage for inserting the optical fiber 7 as well.

The micro-catheter Mc having the optical fiber 7 inserted therein is passed through the interiors of the Y connector 62, the hub 63, and the guiding catheter Gc and extended to the distal end of the guiding catheter Gc. The micro-catheter Mc is provided in the neighborhood of the distal end portion thereof with the laser irradiating part 7a for emitting a laser beam. Incidentally, the micro-catheter Mc is preferred to be such that the portion thereof extending from the proximal part connected to the hub 61 to the laser irradiating part 7a possesses comparatively high stiffness from the viewpoint of efficiency of operation, and the portion thereof extending from the laser irradiating part 7a to the distal end portion constitutes a flexible distal part 7b for the purpose of preventing itself from inflicting a scratch on the inner surface of the blood vessel during the insertion into the patient's body.

In this embodiment, the leading terminal part of the micro-catheter Mc is provided in the lateral face thereof (tube wall surface) with an opening part 70 as illustrated in FIG. 9. Though this opening part 70, the guiding catheter Gc and the micro-catheter Mc are allowed to communicate in the radial direction.

The laser irradiating part 7a is provided in a reinforcing member 71 on the inner surface of the micro-catheter Mc and consequently enabled to prevent the comparatively soft micro-catheter Mc from being directly affected by high temperature and the pressing power induced by the generation of the bubble B. The reinforcing member 71 may be made of any high melting material which is capable of fitting the inner surface of the micro-catheter Mc and withstanding the heat of the laser beam. Commendably, it is a metallic sleeve of stainless steel, tungsten, nickel, or Inconel®, for example. Preferably, the reinforcing member 71 is possessed of a radiopaque marker impervious to the X rays.

The reinforcing member 71 has a stepped part 72 and a projecting part 73 formed at the leading terminal thereof. The stepped part 72 is meant as a stopper during the insertion of the optical fiber 7 into the micro-catheter Mc and the projecting part 73 is meant as a connecting part for the flexible distal part 7b. In the insertion of the optical fiber 7 into the micro-catheter Mc, the irradiating position can be confirmed by obtaining a sensation of the collision of the leading terminal against the stepped part 72. The presence of the projecting part 73 results in facilitating the work of connecting the soft distal part 7b and enabling an artisan to enjoy exaltation of the convenience and the practical effect.

A check valve 75 formed of a heat resisting thin film such as, for example, a resinous film of polyvinylidene chloride is retained as nipped between the opening part 70 of the micro-catheter Mc and an opening part 74 of the reinforcing member 71. The check valve 75 the guiding catheter Gc allows inflow of the liquid W from the interior of the guiding catheter Gc through the interior of the micro-catheter M and checks the flow in the opposite direction. The liquid W which has flown through the gap between the guiding catheter Gc and the micro-catheter Mc, therefore, only flows into the micro-catheter Mc and never flows back. Here, for the sake of ensuring the inflow of the liquid W into the micro-catheter Mc, the opening part 70 is preferred to be positioned more toward the basal terminal side than the leading terminal of the guiding catheter Gc.

Now, the operation of this embodiment will be described below.

First, the artisan, prior to inserting the micro-catheter Mc into the blood vessel, introduces the liquid W through the passage 60 into the micro-catheter Mc till a full capacity and makes it certain that no bubble is present therein. Meanwhile, he inserts the guiding catheter Gc by an ordinary procedure into the blood vessel and keeps the interior of the guiding catheter Gc supplied at all times with the liquid W by means of the syringe pump Kp.

Then, the artisan inserts the guide wire (not shown) through the opening at the rear terminal of the hub 61 into the micro-catheter Mc and, in the same manner as the ordinary procedure, inserts the micro-catheter Mc into the blood vessel along the guide wire, with the guide wire advanced ahead. During this insertion, he keeps the position of the reinforcing material 71 in the living body confirmed with the marker visualized by X-ray radiography.

The artisan, when the micro-catheter Mc arrives at the prescribed position in the blood vessel, extracts the guide wire from the micro-catheter Mc, connects the Y connector 60 to the hub 61, and inserts the optical fiber 7 through the micro-catheter Mc till the leading terminal thereof collides against the stepped part 13 of the reinforcing member 71.

When the laser oscillator 2 is actuated, the pulsated laser beam is passed through the optical fiber 7 and irradiated on the liquid W. The irradiation is effected in the reinforcing member 71, the liquid W is suddenly heated by the pulsated laser beam and the bubble B is intermittently generated. At the result, the liquid W in the reinforcing member 71 is suddenly spouted through the outlet of the reinforcing member 71 and intermittently emitted in the form of the so-called liquid jet J through the soft distal part 7b. Since the check valve 75 checks the outflow of the liquid jet J toward the guiding catheter Gc, the bubble B are prevented from guided from the opening part 70 and the opening part 74 toward the guiding catheter Gc side so that the power of the liquid jet cannot be allayed.

At the same time, the artisan continues to aspirate the liquid W through the passage 60a by the pump P and inject the liquid W through the liquid injecting part 20. Consequently, a flow occurs in the direction opposite the liquid jet J and the shattered thrombus is aspirated together with the blood through the distal side of the micro-catheter Mc.

Since this embodiment manifests the function of shattering the target substance and the function of recovering the shattered substance with one micro-catheter Mc as described above, the catheter can be formed in a smaller diameter and the burden is imposed in a smaller amount on the human body than when the tube for the recovery of the target substance is provided separately.

The aspirated blood is diluted with the liquid W which is flowing through the opening part 70 into the micro-catheter Mc. In this case, since the opening parts 70 and 74 are formed more toward the distal side of the micro-catheter Mc than the leading terminal of the optical fiber 7, the aspirated thrombus and the blood are infallibly diluted with the liquid W before they are exposed to the laser beam of the optical fiber 7. Consequently, the function of shattering the thrombus and the function of aspirating the shattered thrombus can be retained without being allayed because the blood of high concentration is not exposed to the laser beam of the optical fiber 7 and the blood has no possibility of being carbonized and deposited fast on the leading terminal of the optical fiber 7.

As a result, the bubble B generated in the micro-catheter Mc nearly wholly function as the power for pushing the liquid W out and the liquid jet J is spouted toward the thrombus lying ahead, and caused to collide powerfully against the thrombus and, owing partly to the assistance of the thrombus dissolving agent, shatter it, with the result that the circulation of the blood is restarted.

Though the foregoing embodiment contemplate causing the liquid W to flow through one point into the micro-catheter Mc, it is permissible to provide a plurality of opening parts, 70 and 74, for example, and effect the inflow of the liquid W through the plurality of points.

Now, modified examples of the reinforcing member 71 will be explained as the seventh~10th embodiment below. The same component members as shown in the preceding embodiment mentioned above will be denoted by the same reference numerals and their explanation will be omitted.

Seventh Embodiment

Figure 11:
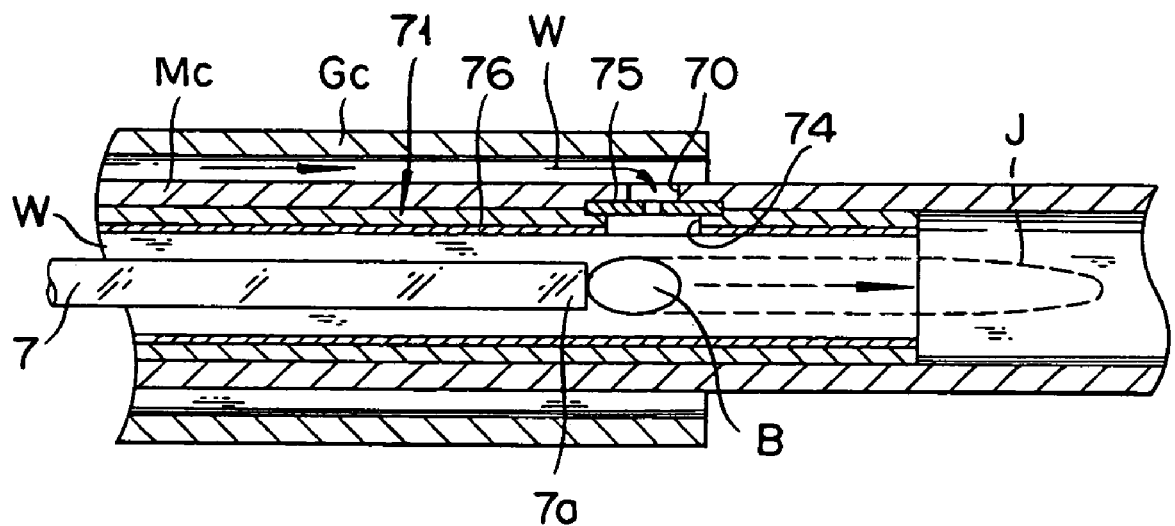
FIG. 11 is a cross section of a catheter depicting the seventh embodiment of this invention.

The reinforcing member 71 of the seventh embodiment, as illustrated in FIG. 11, has formed on the inner surface of the reinforcing member 71 a light reflecting layer 76 capable of reflecting the laser beam irradiated from the optical fiber 7. The formation of the light reflecting layer 76, similarly to the treatment shown in the foregoing embodiment, brings the effect of heightening the efficiency of utilization of the laser beam owing to the prevention of the diffusion of the laser beam and exalting the power of the flow of liquid jet. The reflecting layer 76, however, is required to be provided with the openings 70 and 74 lest it should interfere with the inflow of the liquid W into the micro-catheter Mc.

When the marker which permits easy discrimination of the position of the laser irradiation is used, however, the straight-tube reinforcing member 71 having neither a stepped part 72 nor a projecting part 73 may be effectively used instead.

Eighth Embodiment

Figure 12:
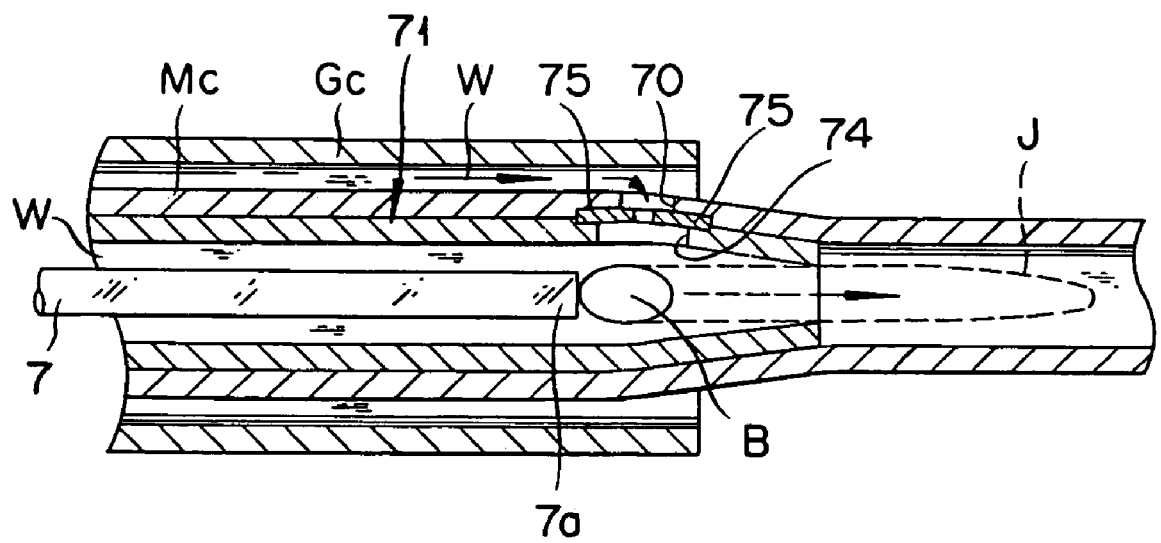
FIG. 12 is a cross section of a catheter depicting the eighth embodiment of this invention.

Though the reinforcing member 71 contemplated by the seventh embodiment is a straight tube having a circular cross section, it does not need to be limited to the straight tube. It may be tapered toward the leading terminal as illustrated in FIG. 12 or formed in a special shape having a rectangular or elliptic cross section.

When the reinforcing member 71 is formed in a tapered shape so as to decrease the inner diameter toward the leading terminal thereof, the taper results in further heightening the rate of speed of the liquid jet J, further adding to the spurting power directed toward the thrombus, and exalting the ability of shattering the thrombus. The same hold good with the tube having different diameters between the opposite sides.

Ninth Embodiment

Figure 13:
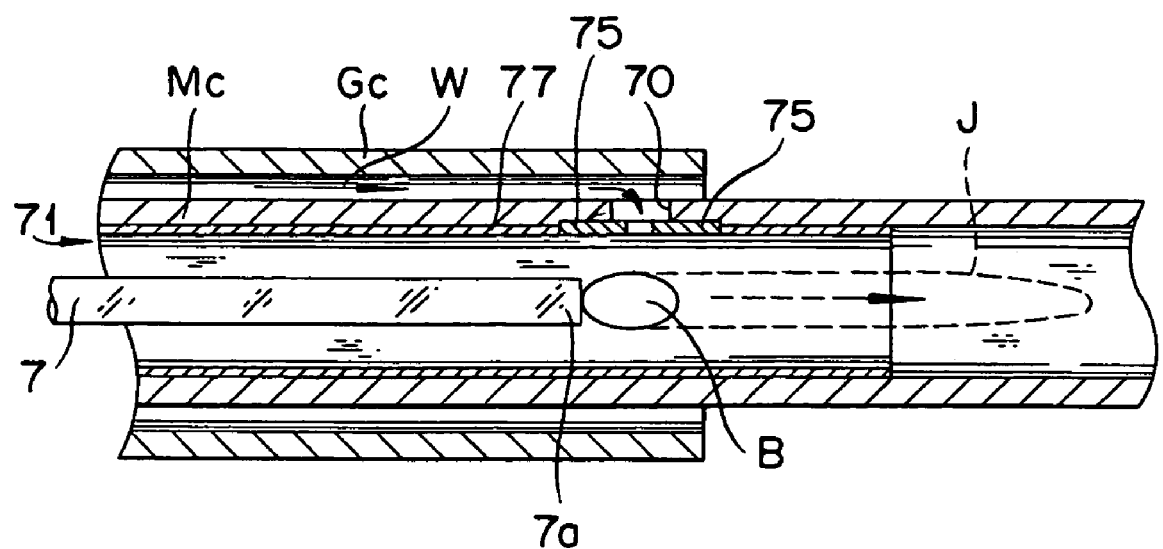
FIG. 13 is a cross section of a catheter depicting the ninth embodiment of this invention.

The reinforcing member 71 contemplated by the preceding embodiment is disposed on the inner surface of the micro-catheter Mc. Since the reinforcing member 71 in this embodiment is required to possess a high melting point enough to withstand the heat generated by the optical fiber 7 and exhibit prescribed stiffness, it assumes the shape of a protective film layer 77 formed directly on the inner surface of the micro-catheter Mc as illustrated in FIG. 13.

The protective film layer 77 is formed in the same manner as used for the light reflecting layer 76 mentioned above by performing a pertinent treatment directly on the inner surface of the micro-catheter Mc. When the protective film layer 77 is formed, the check valve 75 can be strongly retained between the micro-catheter Mc and the protective film layer 77 by having the check valve 75 attached in advance to the micro-catheter Mc.

Tenth Embodiment

Figure 14:
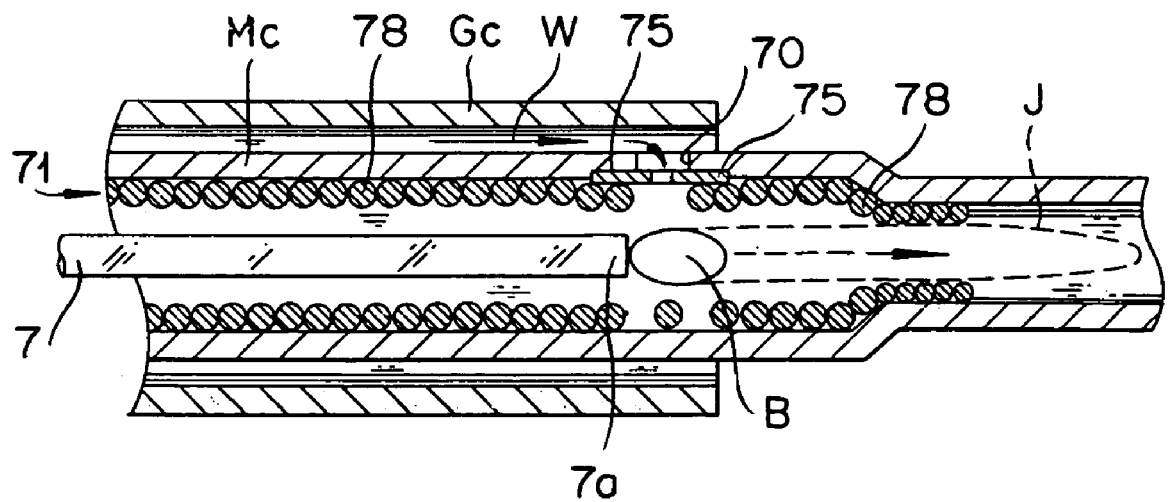
FIG. 14 is a cross section of a catheter depicting the tenth embodiment of this invention.

The reinforcing member 71 contemplated by the preceding embodiment is a metallic sleeve of a small wall thickness or the protective film layer 77 disposed on the inner surface of the micro-catheter Mc. It has the possibility of impeding, though partly, the flexibility of the micro-catheter Mc. The reinforcing member 71 of this embodiment, therefore, is formed of a coiled member 78 as illustrated in FIG. 14.

The coiled member 78 is specifically formed by winding a stainless steel ribbon or piano wire having a thickness or a diameter in the range of 0.001 mm–0.5 mm in the shape of a coil encircling an empty space. It may be formed wholly or partially of an X-ray impervious material so as to function as an X-ray shadowing marker. The leading terminal of the coiled member 78 or part of the coil thereof may be radially converged so that the coiled member 78 may function as a stopper against which the leading terminal part of the optical fiber 7 mentioned above collides. Further, the micro-catheter Mc may be provided in the stiff proximal part thereof with the coiled member 78 so as to impart relatively high stiffness to the micro-catheter Mc and heighten the efficiency of operation thereof. That is, the whole micro-catheter Mc extending from the nearby operating part 52 through the laser irradiating part 7a may be provided with the coiled member 78. This construction, during the course of manipulation, enables the nearby operating part 51 and the micro-catheter Mc to resist such external powers as displacement and torsion in the direction perpendicular to the axis which are exerted thereon, prevents the catheter from being bent or fractured either wholly or to an extent of repression, and precludes the micro-catheter Mc from giving rise to a kink or fracture.

Eleventh Embodiment

While the foregoing embodiment contemplates disposing a passage for the liquid W and a passage for transfusion separately of each other by inserting the micro-catheter Mc in the guiding catheter Gc and forming the interior of the guiding catheter Gc in a two-layer construction, this embodiment contemplates having two passages formed in advance in the catheter 9 and utilizing one of the passages for supplying the liquid W and the remainder for the aspiration of the thrombus.

Figure 15:
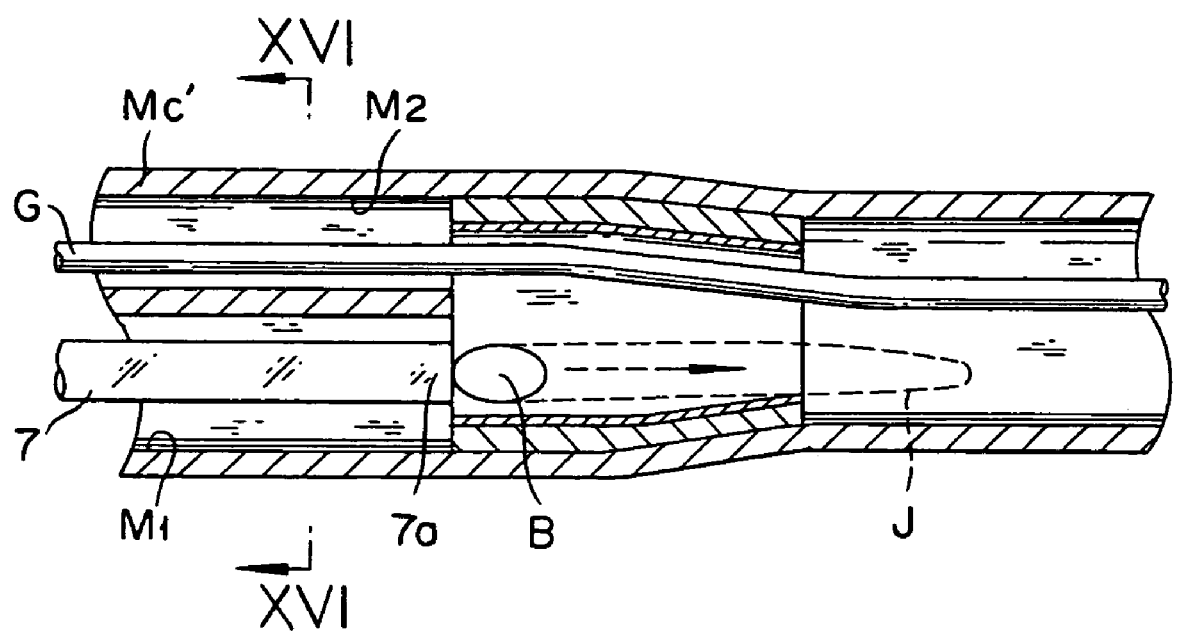
FIG. 15 is a cross section of the leading terminal of a catheter depicting the eleventh embodiment of this invention.
Figure 16:
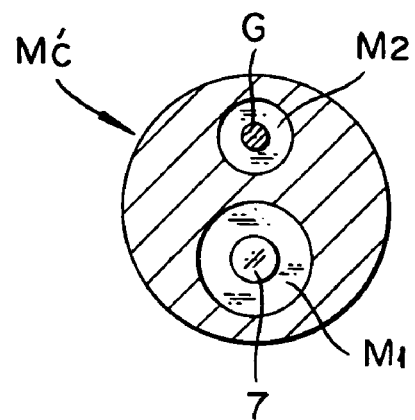
FIG. 16 is a cross section taken through FIG. 15 along the line XVI-XVI.

In FIG. 15 and FIG. 16, a micro-catheter Mc' according to the eleventh embodiment has a passage M1 and a passage M2 formed in the interior thereof. The optical fiber 7 is inserted in the passage M1 and the guide wire G is inserted in the passage M2. The guide wire G is used till the distal end of the micro-catheter Mc' reaches the prescribed position in the blood vessel and subsequently extracted from the passage M2.

When the optical fiber 7 spouts the jet J toward the thrombus lying ahead, the liquid W is supplied to the passage M1 and the liquid W is continuously supplied to the leading terminal of the optical fiber 7. Then, in the passage M2, the thrombus is recovered by the aspiration which is effected by the pump P. The supply of the liquid W and the aspiration for the recovery of the thrombus are carried out by the operation of the nearby operating part 51.

Figure 17:
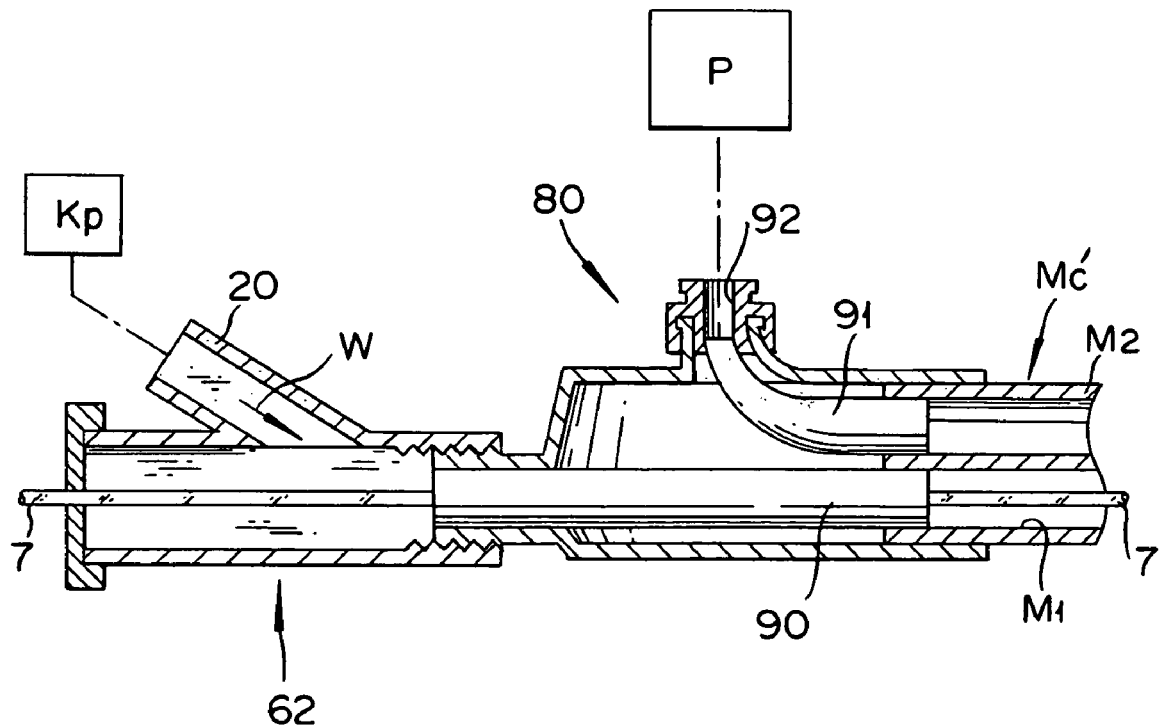
FIG. 17 is a cross section of the nearby operating part.

The nearby operating part 51, as illustrated in FIG. 17, uses a joint member 80 in the place of the Y connector 51 shown in FIG. 8. The joint member 80 is intended to establish connection between the Y-shaped adapter 60 and the micro-catheter Mc' and is provided in the interior thereof with two cylindrical tubes 90 and 91.

The tube 90 tightly connects the Y-shaped adapter 60 and the micro-catheter Mc', effects the inflow of the liquid W into the passage M1 by means of the syringe pump Kp disposed in the liquid injecting part 20 of the Y-shaped adapter 62, and guides the liquid to the distal end portion of the micro-catheter Mc'.

The tube 91 tightly connects a suction inlet 92 and the micro-catheter Mc' and fulfills the function of filling the micro-catheter Mc' with the liquid W by means of the pump P and the function of aspirating the liquid W containing the shattered thrombus, for example.

By forming the passage for the supply of the liquid W and the passage for the recovery of the thrombus in one micro-catheter Mc' as described above, it is made possible to form the catheter in a smaller diameter and allow the burden to be imposed in a smaller amount on the human body than when the tube for the recovery of the target substance is provided separately.

This invention does not need to be limited only to the various modes of embodiment described above but may be variously altered by a person of ordinary skill in the art within the technical idea of this invention. The laser induced liquid jet generating apparatus described above is used not only for shattering the thrombus but also for implementing other purposes such as, for example, a laser surgical knife.

What is claimed is:

1. A laser induced liquid jet generating apparatus comprising:
   a main body possessing a spatial part therein,
   an optical fiber fitting part disposed to communicate with the spatial part of said main body, and intended to fit an optical fiber furnished with a laser irradiating part for allowing introduction of a laser beam from a laser oscillator into the spatial part,
   a liquid injecting part for injecting into the spatial part of said main body a prescribed liquid capable of absorbing said laser beam, and
   a nozzle disposed at said main body for spouting a liquid jet generated when the liquid is irradiated by said laser beam emitted from the laser irradiating part toward said liquid to the exterior of said main body, and
   a catheter communicating with the nozzle, the nozzle guiding the liquid jet generated in the spatial part of said main body into a proximal end portion of the catheter.

2. An apparatus according to claim 1, wherein said main body has said liquid injecting part disposed to direct said liquid toward the laser irradiating part of said optical fiber.

3. An apparatus according to claim 1, wherein said main body is provided with a liquid discharging part for discharging said liquid to the exterior of said main body.

4. An apparatus according to claim 1, wherein said main body is disposed at a position between a distal end portion of said optical fiber fitting part and the nozzle so that the distal end portion of said optical fiber fitting part and the nozzle oppose each other.

5. An apparatus according to claim 4, wherein an inner wall surface of said spatial part is tapered to decrease the inner diameter of said spatial part from the optical fiber fitting part side toward the nozzle.

6. An apparatus according to claim 1, wherein said main body is formed of a material having a melting point high enough to withstand the heat generated by said optical fiber and possessing stiffness.

7. An apparatus according to claim 6, wherein the material of said main body is a metal.

8. An apparatus according to claim 1, wherein said main body has an inner wall surface of said spatial part provided with a reflecting layer capable of reflecting the laser beam emitted from the laser irradiating part of said optical fiber.

9. An apparatus according to claim 1, wherein said spatial part in the neighborhood of the position for irradiating the laser beam from said optical fiber is at least provided with a reinforcing member formed of a material having a melting point high enough to withstand the heat generated by said optical fiber and possessing stiffness.

10. An apparatus according to claim 9, wherein said reinforcing member is provided on an inner surface thereof with a reflecting layer capable of reflecting the laser beam emitted from said optical fiber.

11. An apparatus according to claim 1, wherein said main body comprises a first main body and a second main body capable of being connected to a proximal end portion of said first main body, said first main body comprising:
a first spatial part formed in an interior thereof,
a liquid discharging part communicating with said first spatial part for discharging the liquid from the interior of said first spatial part,
the nozzle disposed in a distal end portion of said first main body for spouting the liquid in said first spatial part to the exterior of said first main body, and
a first connecting part disposed in the proximal end portion of said first main body and provided with an first opening part communicating with said first spatial part, said second main body comprising:
a second spatial part formed therein,
a second connecting part, which has a second opening part disposed in a distal end portion of said second main body and communicating with said second spatial part, being capable of connecting to said first connecting part in a state allowing said first spatial part and second spatial part to communicate with each other through said second opening part,
the optical fiber fitting part disposed to communicate with said second spatial part,
and said liquid injecting part for injecting the liquid into said second spatial part.

12. An apparatus according to claim 11, wherein said main body is furnished in said first spatial part with a partition tube having an interior thereof communicating with said first opening part of said first connecting part and allowing insertion therein of the optical fiber attached to said optical fiber fitting part.

13. An apparatus according to claim 12, wherein said partitioning tube is extended more toward said nozzle than the basal part of said liquid discharging part.

14. An apparatus according to claim 12, wherein said partitioning tube is formed of a material having a melting point high enough to withstand the heat generated by said optical fiber and possessing a prescribed stiffness.

15. A laser induced liquid jet generating apparatus comprising:
a main body having a spatial part formed in an interior thereof,
a liquid discharging part communicating with the spatial part of said main body for discharging a liquid in said spatial part,
a nozzle disposed in a distal end portion of said main body and adapted to spout the liquid in said spatial part to the exterior of said main body, and
a connecting part disposed in a proximal end portion of said main body, furnished with an opening part communicating with said spatial part, and furnished with an optical fiber fitting part and a liquid injecting part, wherein
the liquid injected from the liquid injecting part of said connecting part is guided into said spatial part of said main body through the medium of said opening part,
a liquid jet generated by irradiating the liquid with a laser beam emitted from an optical fiber attached to said optical fiber fitting part toward the liquid in said spatial part is guided into a proximal end portion of a catheter connected to said nozzle, and the liquid jet is spurt to a distal end portion of said catheter.

16. An apparatus according to claim 1, wherein the irradiation of the laser beam occurs in the main body and not in the catheter.

* * * * *